United States Patent
Odogba et al.

(10) Patent No.: US 6,404,853 B1
(45) Date of Patent: Jun. 11, 2002

(54) METHOD FOR IDENTIFYING AND CORRECTING PIXELS WITH EXCESS PIXEL LAG IN A SOLID STATE X-RAY DETECTOR

(75) Inventors: Jibril Odogba; Kenneth Scott Kump; John Moore Boudry, all of Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/682,961
(22) Filed: Nov. 2, 2001
(51) Int. Cl.[7] .................................................. H05G 1/64
(52) U.S. Cl. ..................... 378/98.8; 378/207; 250/208.1
(58) Field of Search ................................. 348/241, 246, 348/247, 180, 187, 207; 378/19, 91, 98.8, 207; 382/254, 132; 250/208.1

(56) References Cited

U.S. PATENT DOCUMENTS

| | | | |
|---|---|---|---|
| 4,996,413 A | 2/1991 | McDaniel et al. | 250/208.1 |
| 5,657,400 A | 8/1997 | Granfors et al. | 382/254 |
| 5,970,115 A * | 10/1999 | Colbeth et al. | 378/62 |
| 6,118,846 A * | 9/2000 | Liu | 378/62 |
| 6,296,387 B1 * | 10/2001 | Guillemaud | 378/207 |

* cited by examiner

*Primary Examiner*—Robert H. Kim
*Assistant Examiner*—Therese Barber
(74) *Attorney, Agent, or Firm*—McAndrews, Held & Malloy, Ltd.; Peter J. Vogel; Michael A. Dellapenna

(57) ABSTRACT

A method is provided to identify pixels in a digital x-ray detector that experience an amount of residual charge that is sufficient to cause an image artifact. A lag artifact threshold is obtained. The lag artifact threshold identifies an amount of residual charge that, when held by the pixels in the digital x-ray detector, will cause image artifacts. A pixel lag experienced by a pixel is determined. The pixel lag may be different for each pixel. Pixels that have a pixel lag exceeding the lag artifact threshold are identified and corrected.

23 Claims, 4 Drawing Sheets

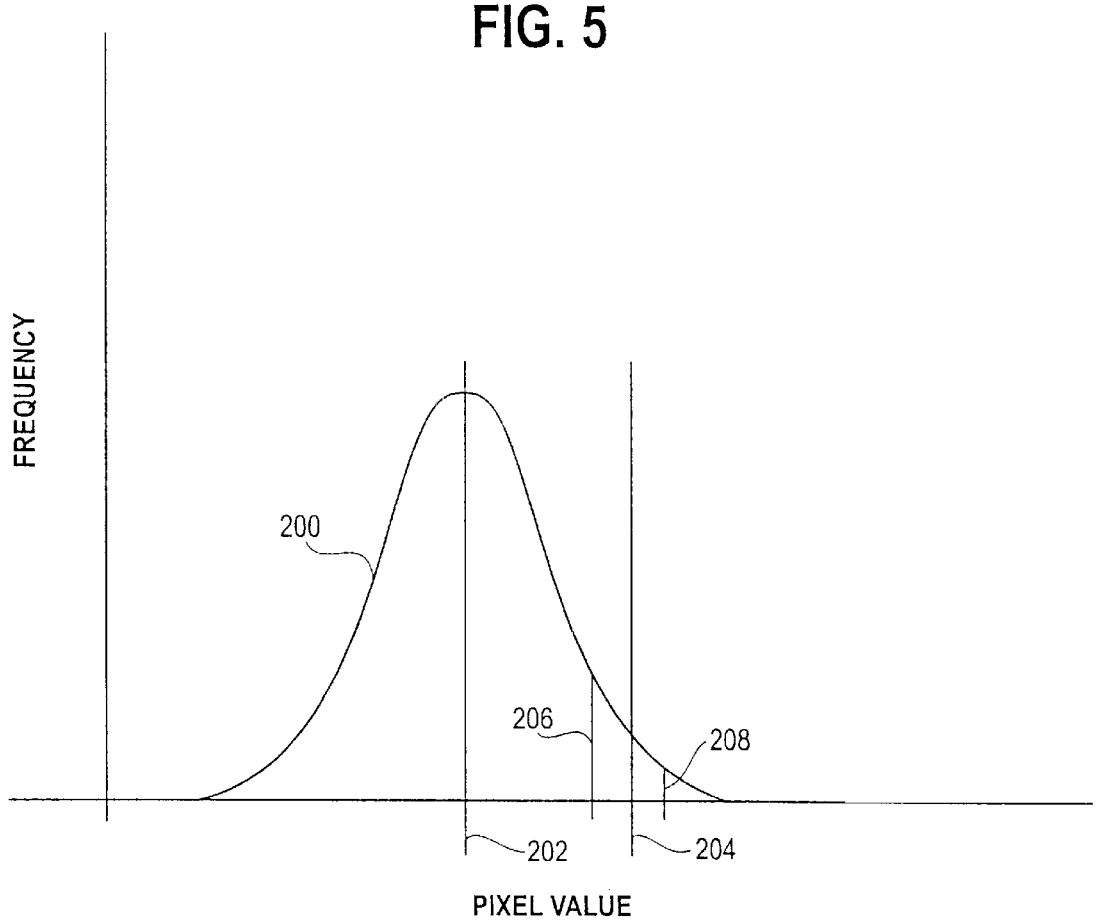

METHOD FOR IDENTIFYING AND CORRECTING PIXELS WITH EXCESS PIXEL LAG IN A SOLID STATE X-RAY DETECTOR

BACKGROUND OF INVENTION

Certain embodiments of the present invention relate to x-ray systems utilizing a solid state multiple element x-ray detector for producing an image, and in particular, to techniques and apparatus for identifying pixels susceptible to artifacts caused by excess pixel lag and for correcting the artifacts.

Solid state x-ray detectors are being developed that comprise a two dimensional array, typically of 1,000 to 4,000 detector elements in each dimension (x,y). Each detector element comprises a photo detector that detects and stores charge representative of an amount of radiation incident on the detector element. Each detector element further includes a thin film transistor (TFT) connected to the photo diode and operated as a switch to enable and disable read out of the charge stored on the photo diode. Each detector element ultimately produces an electrical signal which corresponds to the brightness of a picture element in the x-ray image projected onto the detector. The signal from each detector element is read out individually and digitized for further image processing, storage and display.

The solid state detector may be used in a variety of x-ray medical imaging applications. One such application is dual-energy imaging. In dual-energy imaging, two sequential x-ray images are acquired very close together in time. One acquisition is typically a low energy image (i.e. an image read out after 60–90 kVp exposure), while the other acquisition is typically a high energy image (i.e. an image read out after 110–140 kVp exposure). From the two raw input images, an algorithm is executed which creates a first "bone-only" image and a second "soft tissue only" image. This algorithm is known in the art and can take many forms, such as log subtraction. The combination of the two images enhances visualization of nodules and calcifications.

The solid state detector may also be used to acquire a greater number of sequential x-ray images. For example, a large number of images may be acquired to build a cine-loop of a heart. As with the dual-energy imaging described above, the acquisitions are acquired with a short time interval between them. The short time interval helps to reduce artifacts due to patient motion and/or capture the motion of the patient anatomy.

Solid state detectors unfortunately may experience image lag. Image lag is the retention in the detector of imaging information from prior images. For example, lag may be caused by residual charge in the photo diode or TFT of a detector element. The charge from a second or subsequent exposure is added to the residual charge, or lag, increasing the pixel's signal output. For solid state detectors, the degrading effects due to lag generally increase with decreasing time between image acquisitions, and/or the number of consecutive images.

An individual pixel experiencing excessive lag may appear to have a significantly different signal than some or all of its neighboring pixels and exhibit an artifact. For example, pixels experiencing more lag than neighboring pixels may look brighter while pixels experiencing less lag than neighboring pixels may look darker, even though each of the pixels have received the same level of radiation. The artifacts may be any size or shape, for example, point artifacts, line segments, or rectangular regions. The artifacts may simply be bothersome to a clinician, or may potentially impact a patient diagnosis.

In the past, image lag has been characterized by the average lag of the detector. A detector with average lag falling within a predefined range was considered good, or acceptable for clinical use. A detector with average lag falling outside the predefined range was identified as not acceptable for clinical use and scrapped. Unfortunately, previous methods were unsuccessful at detecting and correcting individual pixels, lines, and other arbitrary artifacts due to lag uniformity problems.

Therefore, it is desirable to identify which pixels, because of excessive lag, present an unacceptable risk for exhibiting artifacts.

SUMMARY OF INVENTION

In accordance with at least one embodiment, a method is provided for identifying, in a digital x-ray detector, pixels that retain an amount of charge sufficient to cause an image artifact. In accordance with the method, a lag artifact threshold is obtained which identifies the amount of residual charge that will cause image artifacts. Optionally, the lag artifact threshold may be representative of a percent confidence that the pixel will not exhibit an image artifact. Alternatively, the lag artifact threshold may be obtained by using a perception value determined by perception studies utilized to identify image artifacts. The difference between the perception value and the percent confidence may also be utilized to obtain the lag artifact threshold.

The pixel lag experienced by a pixel in the detector is determined. Optionally, the pixel lag may represent the amount of residual charge held by a pixel. Alternatively, a median pixel lag may be computed based upon the amount of lag experienced by a group of pixels surrounding the pixel. In one instance, the group of pixels may define a region of pixels one square centimeter surrounding the pixel. It is possible that an excess pixel lag, representing the amount of lag that the pixel experiences which is greater than the median pixel lag, may be computed. Pixels retaining pixel lag in excess of the lag artifact threshold are then identified. Additionally, a noise value representative of the noise experienced by the detector may be identified. The noise value may be utilized, together with the radiation level, to which the detector was exposed, to calculate the excess pixel lag. The pixels experiencing lag in excess of the lag artifact threshold may be used to generate a lag pixel artifact map.

In accordance with an alternative embodiment, the digital x-ray detector may be exposed to a first radiation level. A first set of signals representing the first radiation level may be obtained. The detector may then be exposed to a second radiation level, and a second set of signals may be obtained. It is possible that the first radiation level is a high level, and the second radiation level is a low level. The lag artifact threshold may be based upon the first and second radiation levels. The amount of lag experienced by the pixel in excess of the average lag experienced by the surrounding pixels may be calculated using the two radiation levels.

In accordance with at least one embodiment, a method is provided for calculating a lag pixel artifact map for a digital x-ray detector. The detector is exposed to radiation. Then the detector is read consecutively to obtain at least first and second sets of pixel values. Optionally, the first and second sets of pixel values are acquired within a predetermined time of each other, such as 200 ms. A lag artifact threshold identifying the amount of residual charge held by pixels in the detector that may cause image artifacts is obtained. Alternatively, the lag artifact threshold may be representative of a percent confidence that the pixel will not exhibit an image artifact.

Excess pixel lag may also be calculated for a pixel in the detector. Optionally, a perception value determined by perception studies utilized to identify image artifacts may be used to calculate the excess pixel lag. The excess pixel lag may be calculated by utilizing a ratio of the retained charge on a current pixel and the average retained charged for a set of pixels surrounding the current pixel. Additionally, a noise value may be determined for the noise that is experienced by the detector. The noise value may be utilized, together with the radiation level, to which the detector was exposed, to calculate the excess pixel lag. The excess pixel lag is compared to the lag artifact threshold. If the excess pixel lag is greater than the lag artifact threshold, the pixel is added to a lag pixel artifact map.

By identifying which pixels in the digital x-ray detector may cause image artifacts due to excess lag, the image artifacts may be corrected. This is advantageous as the image artifacts may be distracting to the technician or radiologist who is viewing the x-ray image. Additionally, the presence of image artifacts may lead the radiologist to prescribe additional, unnecessary scans or tests to confirm that the image artifacts are not representative of patient anatomy. The additional scans add to the overall cost and are undesirable as the patient may be exposed to additional radiation.

BRIEF DESCRIPTION OF DRAWINGS

FIG. 5 illustrates a distribution of pixel values used to calculate median pixel lag in accordance with an embodiment of the present invention.

The foregoing summary, as well as the following detailed description of the embodiments of the present invention, will be better understood when read in conjunction with the appended drawings. It should be understood, however, that the present invention is not limited to the arrangements and instrumentality shown in the attached drawings.

DETAILED DESCRIPTION

Figure 1:
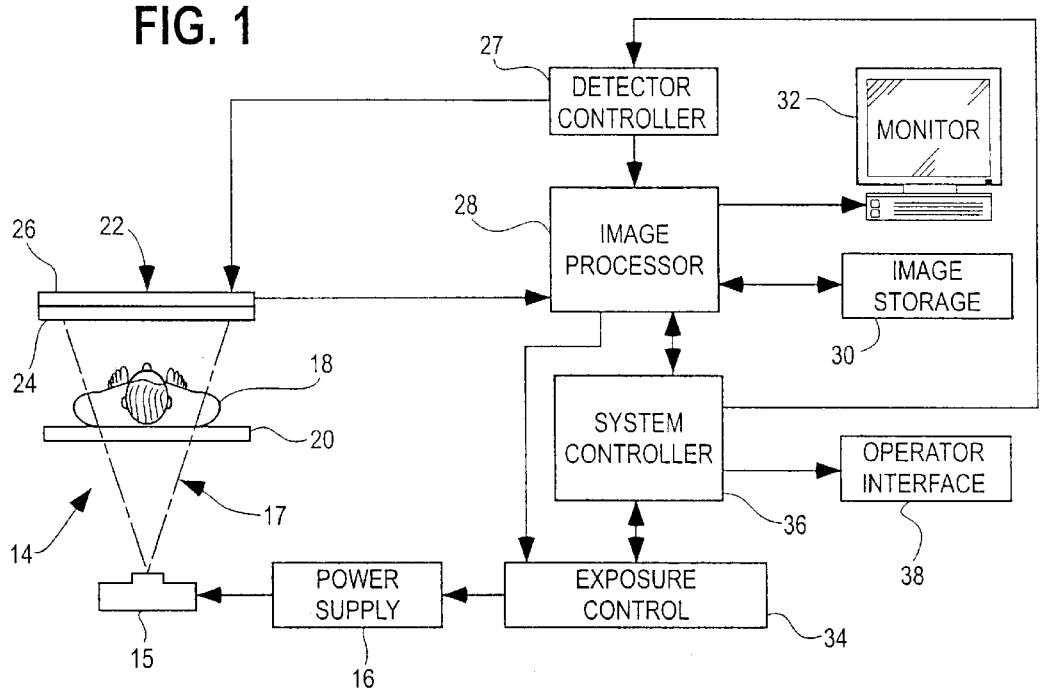
FIG. 1 illustrates a high level diagram of an x-ray imaging system in accordance with an embodiment of the present invention.

With initial reference to FIG. 1, an x-ray apparatus 14 includes an x-ray tube 15 which, when excited by a power supply 16, emits an x-ray beam 17. As illustrated, the x-ray beam 17 is directed toward a patient 18 lying on an x-ray transmissive table 20. The portion of the beam 17 which is transmitted through the table 20 and the patient 18 impinges upon an x-ray detector designated 22. The x-ray detector 22 comprises a scintillator 24 that converts the x-ray photons to lower energy photons, i.e., light photons. Contiguous with the scintillator 24 is a photodetector array 26, which converts the light photons into an electrical signal. A detector controller 27 contains electronics for operating the detector array to acquire an image and to read out the signal from each photodetector element.

The output signal from the photodetector array 26 is coupled to an image processor 28 that includes circuitry for processing and enhancing the x-ray image signal. The processed image then is displayed on a video monitor 32 and may be archived in an image storage device 30. The image processor 28 additionally produces a brightness control signal which is applied to an exposure control circuit 34 to regulate the power supply 16 and thereby the x-ray exposure. The overall operation of the x-ray apparatus 14 is governed by a system controller 36 which receives commands from the x-ray technician via an operator interface panel 38.

Figure 2:
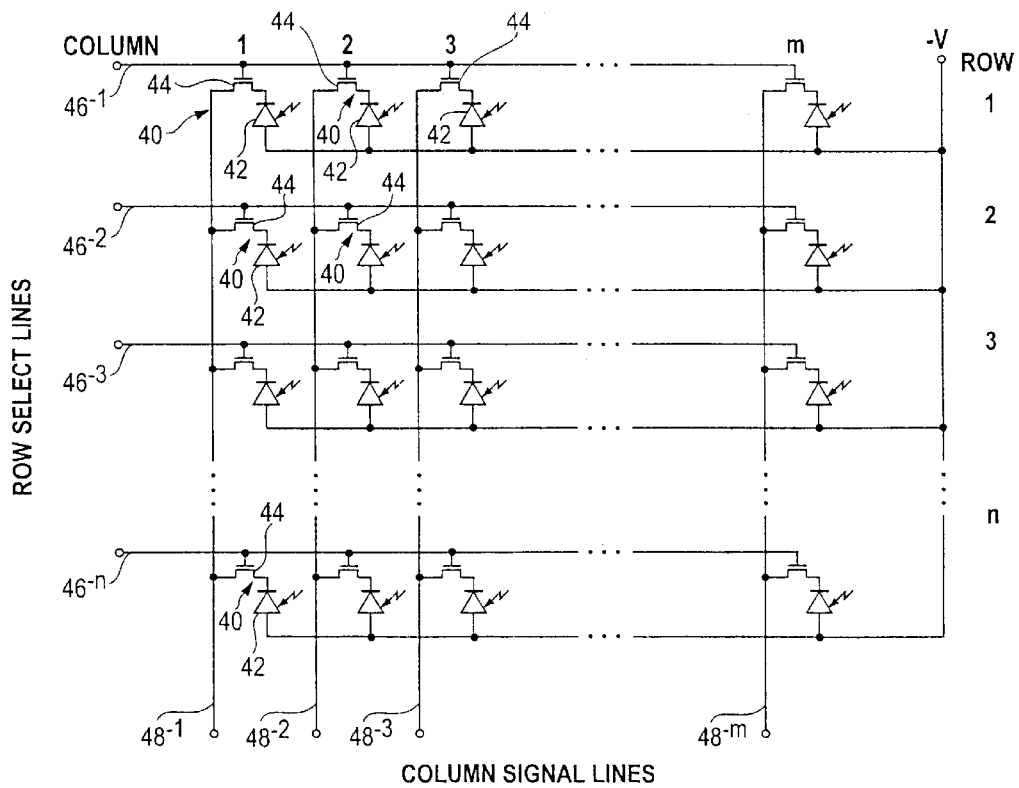
FIG. 2 illustrates circuitry of the photodetector array in accordance with an embodiment of the present invention.

FIG. 2 illustrates the circuitry of the photodetector array 26, which is formed by a matrix of detector elements 40. The detector elements 40 are arranged on an amorphous silicon wafer in a conventional two-dimensional array of m columns and n rows, where m and n are integers. For example, a typical high resolution x-ray detector is a square array of 1,000 to 4,000 rows and columns of elements. Each detector element 40 includes a photo diode 42 and a thin film transistor (TFT) 44. The photo diodes 42 are fabricated from a large wafer area in order that the photo diode 42 will intercept a sizeable portion of the light produced by the scintillator 24. Each photo diode 42 also has a relatively large capacitance that allows it to store the electrical charge resulting from the photon excitation.

The cathode of the photo diodes 42 in each column of the array 26 is connected by the source-drain conduction path of the associated TFT 44 to a common column signal line ($48^{-1}$ through $48^{-m}$) for the column. For example the photo diodes 42 in column 1 are coupled to the first signal line $48^{-1}$. The anodes of the diodes in each row are connected in common to a source of a negative bias voltage (–V). The gate electrodes of the TFTs 44 in each row are connected to a common row select line ($46^{-1}$ through $46^{-n}$), such as line $46^{-1}$ for row 1. The row select lines and the column signal lines are coupled to the detector controller 27 and the column signal lines also are connected to the image processor 28.

In order to acquire an x-ray image using the detector 22 illustrated in FIG. 1, the apparatus 14 may perform the following sequence of operations. Initially, the detector controller 27 connects all of the column signal lines ($48^{-1}$ through $48^{-m}$) to ground and applies a positive voltage ($V_{on}$) to all of the rows elect lines ($46^{-1}$ through $46^{-n}$). The positive voltage applied to the row select lines turns on the TFT 44 in each detector element 40 placing a positive charge on the reverse biased photo diodes 42. Once the photo diodes 42 have been fully charged, the detector controller 27 applies a negative voltage ($-V_{off}$), which is more negative than the negative supply voltage (–V), to the row select lines ($46^{-1}$ through $46^{-n}$). This negative biasing of the row select lines turns off the TFT 44 in each detector element 40.

Then the detector 22 is exposed to a pulse of x-ray photons produced in a conventional manner by the system exciting tube 15 to generate a beam 17 of x-ray photons. The x-ray photons are converted to lower energy photons by the scintillator 24. When these lower energy photons strike the photo diodes 42 in the detector 26, the electron-hole pairs are liberated and stored in the capacitance of the photodiode. The amount of charge stored in the given photo diode 42 depends upon the amount of lower energy photons that strike it, which in turn depends upon the intensity of the x-ray energy that strikes the region of the scintillator 24 adjacent to the photo diode. Therefore, the amount of charge stored in the photo diode 42 in each detector element 40 is a function of the x-ray intensity striking the corresponding region of the x-ray detector 22.

After the termination of the x-ray exposure, the residual charge in each photo diode 42 is sensed. To do so, the column signal line ($48^{-1}$ through $48^{-m}$) for each detector array column is simultaneously connected to separate sensing circuits in the image processor 28. Any of several types of sensing circuits can be incorporated into the image processor 28. For example, the sensing circuit can measure the voltage across the photo diode, and therefore the amount of charge stored in the photo diode. Alternatively, the sensing circuit can connect the associated column signal line ($48^{-1}$ through $48^{-m}$) to a lower potential than the cathode of the photodiode and measure the amount of charge that flows to or from the photodiode.

For maximum image resolution, the photo diode charges are sensed a row at a time by the detector controller 27 sequentially applying the positive voltage ($V_{on}$) to each of the row select lines ($46^{-1}$ through $46^{-n}$). When a row select line ($46^{-1}$ through $46^{-n}$) is positively biased, the detector array TFTs 44 connected to that row select line ($46^{-1}$ through $46^{-n}$) are turned on thereby coupling the associated photo diodes 42 in the selected row to their column signal lines ($48^{-1}$ through $48^{-m}$).

Each detector element 40 corresponds to a pixel in the resultant image. Therefore, the level of the photo diode charge determines the value of the corresponding pixel. A pixel's value $P_1$, after offset correction, is proportional to the level of the input exposure $E_1$ as shown in Equation 1:

$$P1 = mE1 - \beta mE1 \qquad \text{Equation 1}$$

wherein $P_1$ is the pixel value, $E_1$ is the input exposure (i.e. kVp), m is the response coefficient, and β is the median pixel lag of the pixels in the region of the detector 22 that surrounds the pixel. The response coefficient m is fixed for a given detector 22 at a given x-ray energy spectrum, and may vary from one detector 22 to another. Thus, if a pixel is exposed to an increased input exposure $E_1$, the pixel value $P_1$ will increase. A pixel exposed multiple times to an input exposure $E_1$ may not produce an identical pixel value $P_1$ for each exposure $E_1$. For example, if pixel "A" is exposed multiple times to a substantially similar input exposure $E_1$, and the exposures are separated in time so that no residual charge is retained in the detector 22, the pixel values $P_1$ for pixel "A" will result in a normal distribution, such as a Gaussian distribution.

A pixel is identified as an artifact if the pixel value P satisfies the following inequality:

$$|P - \mu| > \kappa \sigma_b \qquad \text{Equation 2}$$

wherein $\mu$ is the average value for neighboring pixels, and $\sigma_b$ is the standard deviation value for neighboring pixels and represents the background noise. The area of the detector 22 that defines neighboring pixels is discussed further below. Taking the absolute value of the difference between the pixel value P and the average value $\mu$ allows identification of pixel values P with excessive lag either above or below the mean. The parameter κ is application dependent. As parameter κ becomes larger, less pixels are identified as artifacts.

The value of κ is typically determined through perception studies in which isolated pixels, lines and other artifacts are generated at different signal-to-noise ratios. A typical value of κ is 1, but κ may range between 0.25 and 6 depending upon the application and the size of the artifact being considered. The value of κ may be chosen for a particular detector 22 due to the size and shape of artifacts specific to the detector 22. A smaller value of κ, such as κ=1, may be used, thus providing tighter restrictions on which pixels are considered to be good. Additionally, the x-ray apparatus 14 may use only one value of κ regardless of the application being acquired.

If a second image is acquired very quickly after the first image, such as in dual-energy imaging, the value for a pixel in the second image after offset correction is:

$$P_2 = mE_2 + \beta m(E_1 - E_2) \qquad \text{Equation 3}$$

wherein $P_2$ is the pixel value in the second image, $E_1$ is the exposure level of the first image, $E_2$ is the exposure level of the second image, and β is the median pixel lag of the pixels in the region of the detector 22 that surrounds the pixel. As discussed previously, m is the response coefficient and is fixed for a given detector at a given x-ray energy spectrum. The median pixel lag β, however, may vary across the detector, and thus is calculated over a small area, such as one or two square centimeters. For example, the value for median pixel lag β may be calculated over one square centimeter surrounding the pixel. As illustrated in Equation 3, the lag is proportional to the difference between the exposures $E_1$ and $E_2$ times the median pixel lag β.

A pixel with a lag value beyond a certain visibility threshold may appear as an image artifact, such as a point or line artifact. For a pixel with excess pixel lag, the pixel value may be obtained from:

$$P_2 = mE_2 + (\beta + \gamma)m(E_1 - E_2) \qquad \text{Equation 4}$$

wherein γ denotes excess pixel lag. Excess pixel lag γ represents a specific pixel's deviation from the median pixel lag β, and excess pixel lag γ is pixel dependent (i.e. each pixel may have a different amount of excess pixel lag γ). Excess pixel lag γ may be represented by a positive number if it is greater than the median pixel lag β, or a negative number if it is less than the median pixel lag β.

Figure 3:
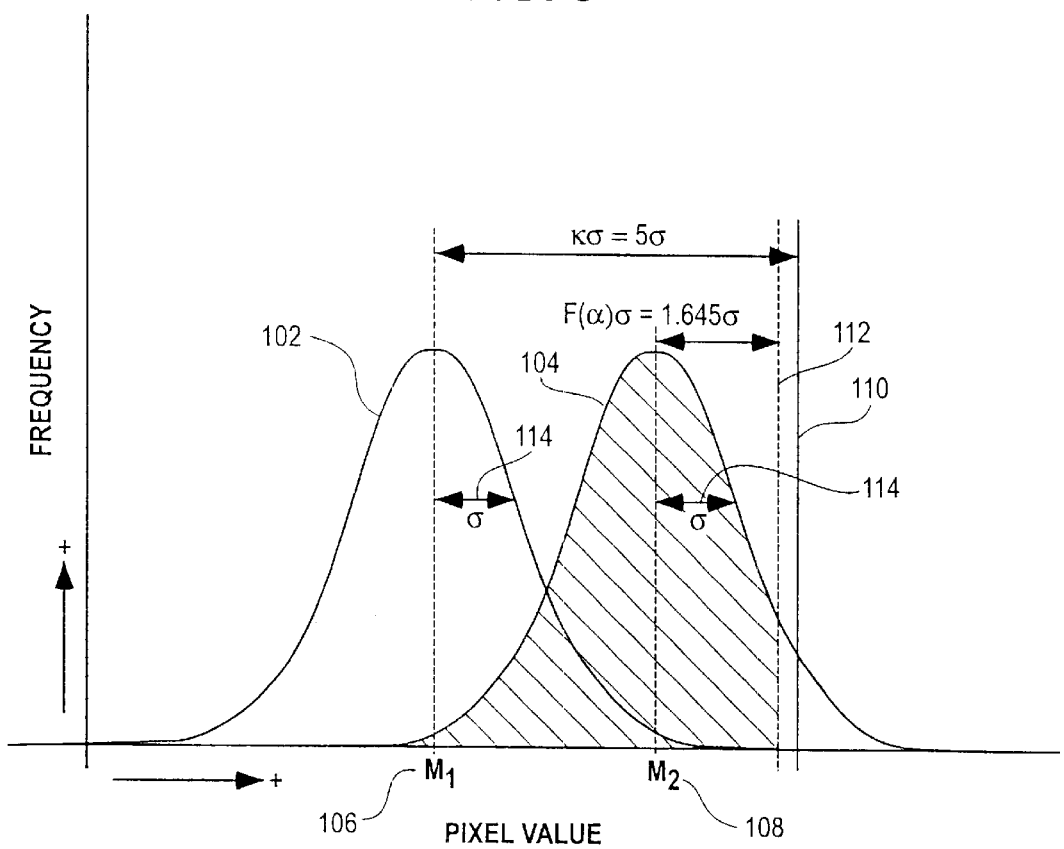
FIG. 3 illustrates a distribution with median pixel lag and a distribution with excess pixel lag in accordance with an embodiment of the present invention.

Although every pixel may experience some level of excess pixel lag γ, not every pixel that experiences excess pixel lag γ will exhibit an artifact. FIG. 3 illustrates the distribution of the response of a pixel with median pixel lag β and the distribution of the response of a pixel with excess pixel lag γ. A pixel with median pixel lag β is represented by the distribution 102. The distribution 102 has a mean value $M_1$ 106. A pixel with excess pixel lag γ is represented by the distribution 104. The distribution 104 has a mean value $M_2$ 108. It should be understood that the distribution 104 represents the absolute value of a pixel with excess pixel lag γ, as excess pixel lag γ may be above or below the median pixel lag β.

The distributions 102 and 104 represent the probability of a pixel value $P_2$ being a given value, as discussed previously in relation to $P_1$, Equation 1, and a normal distribution. The distribution 102 represents the pixel value $P_2$ for a pixel that experiences median pixel lag β compared to its neighboring pixels as expressed in Equation 3. Often, a pixel experiencing median pixel lag β will be at the average, or the mean value $M_1$ 106. The distribution 104 represents the pixel value $P_2$ that experiences median pixel lag β plus excess pixel lag γ compared to its neighboring pixels as expressed in Equation 4. Often, a pixel experiencing excess pixel lag γ will be at the average, or the mean value $M_2$ 108.

For the distribution 104, a percent confidence that the pixel will not be an artifact may be determined. The relationship may be written as:

$$|mE_2+m(\beta+\gamma)(E_1-E_2)+F(\alpha)\sigma|<mE_2+m\beta(E_1-E_2)+\kappa\sigma \quad \text{Equation 5}$$

wherein $\kappa > F(\alpha)$, and $\sigma$ is noise, due to both electronic and quantum noise, and is illustrated in FIG. 3 as noise $\sigma$ 114. A Poisson noise assumption may identify noise $\sigma$ 114 as the square root of the product of the response coefficient m and the input energy E. Alternatively, noise $\sigma$ 114 is experimentally measured and a value is set for a detector 22.

As previously discussed, the value of $\kappa$ is typically determined by perception studies. In FIG. 3, the value of $\kappa$ is 5, although $\kappa$ may be a different number, such as 1, as previously discussed, as long as $\kappa$ is greater than $F(\alpha)$. The mean value $M_1$ 106+$\kappa\sigma$ determines the lag artifact threshold 110 illustrated in FIG. 3. In other words, the lag artifact threshold 110 may be defined by the right side of the relationship in Equation 5. Pixel values $P_2$ that exceed lag artifact threshold 110 may exhibit an artifact.

The term $\alpha$ is the percent confidence that the pixel will not exhibit an artifact, and the function $F(\alpha)$ satisfied the following equation:

$$\alpha = 100 \frac{\sum_{i=0}^{nE_2+(\beta+\gamma)m(E_1-E_2)+F(\alpha)\sigma} N(P_i)}{T} \quad \text{Equation 6}$$

wherein T is the total number of pixels, and $N(P_i)$ is the number of pixels with the pixel value of i. Table 1 lists some exemplary values for function $F(\alpha)$ assuming a Gaussian distribution:

TABLE 1

Values for $F(\alpha)$ as a function of $\alpha$

| $\alpha$ (%) | $F(\alpha)$ |
|---|---|
| 95 | 1.645 |
| 90 | 1.285 |
| 85 | 1.035 |
| 75 | 0.675 |
| 60 | 0.255 |
| 50 | 0 |

The function $F(\alpha)$ does not need to be fixed to any of the values in Table 1, but is typically less then value of $\kappa$. The values for function $F(\alpha)$ may be from any mathematical distribution or may be generated from measured distributions.

By setting percent confidence $\alpha=95$ in Equation 6, a percent confidence threshold 112 is identified FIG. 3. For clarity, the percent confidence threshold 112 is illustrated as a number at pixel values to the left of the lag artifact threshold 110. However, the percent confidence threshold 112 and the lag artifact threshold 110 may be further apart or closer together in pixel value. The cross-hatched area of distribution 104, limited on one side by the distribution percent confidence threshold 112, represents 95% of the total number of pixel values P2 in 104. Therefore, there is a 95% confidence that the pixel with mean value $M_2$ 108 may not exhibit an artifact.

$$\left|\frac{m\gamma(E_1-E_2)}{\sigma}\right| < \kappa - F(\alpha) \quad \text{Equation 7}$$

and Equation 7 may be rewritten as follows:

$$\left|\frac{\gamma \cdot \Delta \text{Signal}}{\sigma}\right| < \kappa - F(\alpha) \quad \text{Equation 8}$$

wherein $\Delta$ Signal is the mean difference in the signal between two consecutive exposures. Equation 7 or 8 may be used to determine an lag artifact threshold (such as line 110 in FIG. 3) on or beyond which the pixel with mean value $M_2$ 108 may exhibit an artifact. In other words, if the value of a pixel in a defined geographic area of the detector (i.e. 1 cm square) is greater than or less than the mean value $M_1$ 106 by a certain number of noise $\sigma$ 114 (i.e. $\kappa\sigma$), the pixel may exhibit an artifact. As illustrated in FIG. 3, a pixel with a value that exceeds the mean value $M_1$ 106 plus 5 $\sigma$, may exhibit an artifact.

Figure 4:
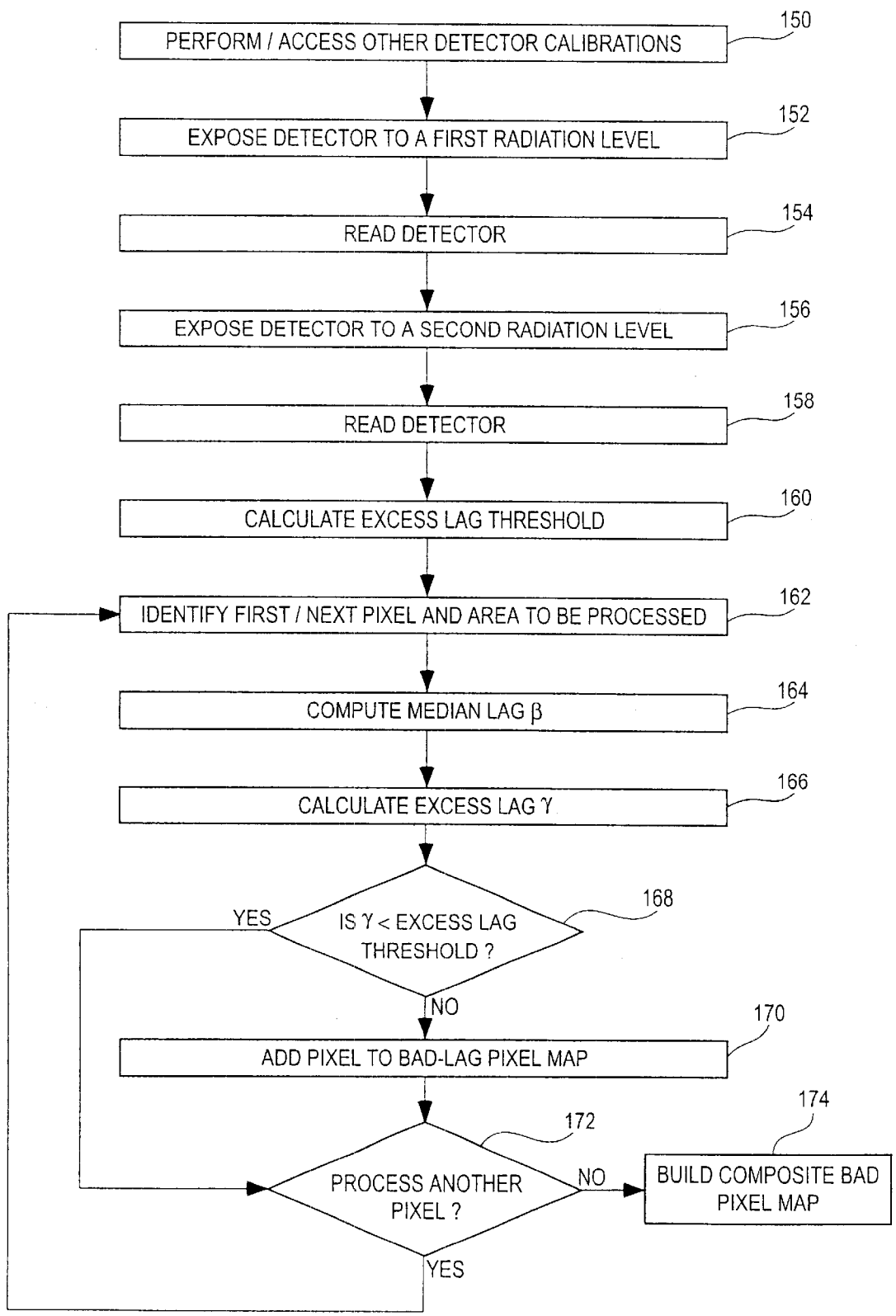
FIG. 4 illustrates a method for identifying and correcting pixels with excess pixel lag in accordance with an embodiment of the present invention.

FIG. 4 illustrates a method for identifying and correcting pixels with excess pixel lag $\gamma$. At step 150, the image processor 28 may perform other detector 22 calibration procedures, such as to identify pixels that do not accurately represent the relationship expressed in Equation 1, and to determine gain correction and the like. The calibration procedures of Step 150 may be accomplished before or after lagging pixels are identified. Pixels identified as bad may be removed from the lagging pixel identification procedure, as further discussed below. Alternatively, the image processor 28 may identify known bad pixels by accessing correction data already stored in the image processor 28.

At step 152, an operator utilizes the system controller 36 to expose the x-ray detector 22 to a first radiation level $E_1$. No collimator, patient 18 or table 20 is placed between the x-ray tube and the detector 22 so that the detector 22 receives a uniform level of radiation. For example, the detector 22 may be exposed to a high level of radiation, such as 110–140 kVp.

At step 154, the image processor 28 reads each of the photo diodes 42 in the detector 22 as previously discussed and the signals are stored in the image processor 28. The signal read from each photo diode 42 represents a pixel value $P_1$, as illustrated in Equation 1.

Next, at step 156, the system controller 36 exposes the detector 22 to a second radiation level $E_2$. The time between the first exposure in step 152 and the second exposure in step 156 is short. By way of example only, no more than 200 ms elapses between the first and second exposures of the detector 22. If too much time passes between the first and second exposures and between the two read operations of the detector 22, the detector 22 may not retain the imaging information (i.e. residual charge) from the first exposure. Thus, the detector 22 may not exhibit the median pixel lag $\beta$ and excess pixel lag $\gamma$ that may be experienced by the detector 22 during normal use if too long of a delay elapses. The kVp level of the second exposure is not important. The second radiation level $E_2$ may be higher than the first radiation level $E_1$, the same as the first radiation level $E_1$, or lower than the first radiation level $E_1$. The second radiation level $E_2$ may be zero. For example, it is possible to skip step 156 and not expose the detector 22 a second time. Additionally, as discussed further below, by not exposing the detector 22 a second time, the excess pixel lag $\gamma$ exhibited by a pixel may be more easily calculated. Therefore, for the remainder of the discussion of FIG. 4, the second radiation level $E_2$ is set to zero.

At step 158, the image processor 28 reads the detector 22 a second time, in the same manner as step 154, and the signals are stored in the image processor 28. The signal level for each photo diode 42 represents a pixel value $P_2$. The pixel value $P_2$ is represented by Equation 3 if the individual pixel exhibits median pixel lag β, or by Equation 4 if the individual pixel exhibits excess pixel lag γ.

At step 160, the image processor 28 computes a lag artifact threshold for a percent confidence β, such as 95%, by using Equation 7 or 8. As median pixel lag β is not used by Equations 7 and 8, a single lag artifact threshold 110 may be calculated for the entire detector 22. The image processor 28 also may calculate the largest value possible for the excess pixel lag γ in Equation 7 or 8 for the computed lag artifact threshold 110.

At step 162, the image processor 28 identifies a first/next pixel and a corresponding region of the detector 22 to be processed. As the median pixel lag β may vary in value over the detector 22 as previously discussed, a region of pixels in the detector 22 surrounding the pixel to be processed is identified. Optionally, the region is 1 cm square.

FIG. 5 illustrates a distribution of pixel values $P_2$ used to calculate median pixel lag β. Distribution 200, median pixel lag β 202, lag artifact threshold 204 (calculated at step 160), and excess pixel lag values 206 and 208 are illustrated. As discussed previously, excess pixel lag γ may be less than the median pixel lag β 202, but a positive value of the excess pixel lag γ is illustrated in FIG. 5 for clarity.

At step 164, the median pixel lag β is computed by finding the median value of the pixel values $P_2$ inside the region identified in step 162. Distribution 200 represents the pixel values $P_2$ inside the region. The pixel values $P_2$ have a median pixel lag β 202. It is possible that one or more pixel values $P_2$ are so much greater or less than the majority of the pixel values $P_2$ in the region that the median pixel lag β 202 calculated using all values of $P_2$ in the region is not representative. Optionally, a more robust median pixel lag β 202 may be calculated by determining an additional threshold that will automatically identify pixels that have pixel values $P_2$ too far from the median and remove the pixel values from the median pixel lag β calculation. Bad pixels may be caused by a malfunction in the detector 22, for example, and may have been identified by other calibration procedures as discussed in step 150.

At step 166, the image processor 28 calculates the excess pixel lag γ for the pixel identified in step 162. As stated previously, the detector 22 is not exposed to a second radiation level (i.e. $E_2=0$). Therefore, by setting $E_2$ equal to 0 and substituting Equation 1 into Equation 4, the image processor 28 may calculate the excess pixel lag using Equation 9:

$$\gamma = \frac{P_2}{P_1} - \beta \qquad \text{Equation 9}$$

Two excess pixel lag γ values 206 and 208 are illustrated in FIG. 5. Each illustrate the excess pixel lag γ for a single pixel as calculated by Equation 9. Excess pixel lag value 206 is below the lag artifact threshold 204, and excess pixel lag value 208 is above the lag artifact threshold 204.

Next, at step 168, the image processor 28 compares the excess pixel lag γ calculated in 166 to the lag artifact threshold 204 identified in step 160. If the excess pixel lag γ is less than the lag artifact threshold 204 (i.e. line 206 in FIG. 5), the pixel will not exhibit an artifact, and control passes to step 172. If the excess pixel lag γ exceeds the lag artifact threshold 204 (i.e. line 208 in FIG. 5), the pixel may exhibit an artifact and control passes to step 170.

At step 170, the image processor 28 adds the pixel to a lag pixel artifact map. The lag pixel artifact map will identify pixels that may exhibit an artifact due to excess pixel lag γ.

For example, the pixel that exhibits excess pixel lag 208 is added to the lag pixel artifact map.

At step 172, the processor 28 determines whether all of the pixels in detector 22 have been processed. If pixels remain to be processed, control passes to step 162, where the next pixel and region are identified. If all of the pixels have been processed, control passes to step 174.

At step 174, the processor 28 combines the lag pixel artifact map with other defective pixel maps (such as maps which may have been created by calibration procedures in step 150) to create a composite defective pixel map. If a pixel is identified as defective by any one of the defective pixel maps, it is identified as defective on the composite defective pixel map. The image processor 28 may correct the pixels identified in the composite defective pixel map by replacing the pixel in the image with an average of the neighboring pixels, for example.

Because the response of the detector element 40 contains noise α, completing the calculation for excess pixel lag γ one time, as illustrated in FIG. 4, may introduce an amount of uncertainty. The noise σ may be due to electronic noise and/or quantum noise. To arrive at a more robust excess pixel lag γ, the method of FIG. 4 may be repeated multiple times (such as 5 times). By repeating the method, the noise σ may be reduced and the percent confidence $F(\alpha)$ may improve. Additionally, FIG. 4 may be repeated using a different value of κ in order to identify pixels susceptible to image artifacts of different sizes and shapes.

Alternatively, the method of FIG. 4 may be modified. The detector may be exposed to radiation, such as in Step 152, then the detector is read 1 to N times, by repeating Step 154. In one embodiment, N is 5, but N may be any number larger than 2. Each read of the detector 2 through N is then compared to the first read of the detector by repeating Steps 160–172. The lag pixel artifact map may then be created by averaging the excess pixel lag γ calculated for each read of the detector 2 through N for each pixel. Alternatively, the lag pixel artifact map may be created by identifying pixels that exhibit excess pixel lag γ for one or more calculations.

Optionally, the method of FIG. 4 may be modified to expose the detector to radiation multiple times. For example, the steps 152–158 may be repeated multiple times, and multiple images may be acquired. The steps 160–172 may then be repeated using the first and second images, the second and third images, the third and fourth images, and so on. As discussed above, the lag pixel artifact map may be created by averaging the excess pixel lag γ calculated for each set of images, or by identifying all pixels that exhibit excess pixel lag γ in any one set of images.

Artifacts caused by pixels with excess pixel lag γ may be distracting to the radiologist, or may possibly result in the patient undergoing additional, unnecessary scans. In extreme cases, the artifacts may result in an erroneous diagnosis. By identifying pixels in a digital x-ray detector that experience an excessive amount of lag, artifacts may be corrected before the image is viewed by a technician or radiologist. Therefore, an image free from artifacts caused by excess pixel lag γ may be evaluated.

While the invention has been described with reference to at least one embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for identifying, in a digital x-ray detector, pixels experiencing an amount of residual charge sufficient to cause an image artifact in images derived from an output of the digital x-ray detector, the method comprising:

obtaining a lag artifact threshold identifying an amount of residual charge that, when held by pixels in a digital x-ray detector, will cause image artifacts;

determining a pixel lag experienced by pixels in the digital x-ray detector; and identifying pixels in the digital x-ray detector having pixel lag exceeding said lag artifact threshold.

2. The method of claim 1, wherein said pixel lag represents an amount of residual charge held by a corresponding pixel.

3. The method of claim 1, wherein the determining step includes computing a median pixel lag based on an amount of lag experienced by a group of pixels in a selected area surrounding a selected pixel.

4. The method of claim 1, wherein the determining step includes computing an excess pixel lag for a selected pixel, said excess pixel lag representing an amount of lag exceeding a median pixel lag for a group of pixels surrounding a selected pixel.

5. The method of claim 1, wherein said lag artifact threshold is representative of a percent confidence that said pixels will not exhibit an image artifact.

6. The method of claim 1, further comprising generating a lag pixel artifact map based on said pixels identified to have said pixel lag exceeding said lag artifact threshold.

7. The method of claim 1, said obtaining step further comprising obtaining a perception value determined by perception studies utilized to identify image artifacts.

8. The method of claim 1, said obtaining step further comprising obtaining a perception value determined by perception studies utilized to identify image artifacts, wherein said lag artifact threshold represents a difference between said perception value and a percent confidence.

9. The method of claim 1, said determining step further comprising identifying a region of pixels surrounding a selected pixel, wherein said region of pixels is utilized to compute a median pixel lag.

10. The method of claim 1, further comprising identifying a noise value representative of noise experienced by said detector, wherein said noise value is utilized to calculate an excess pixel lag for said pixels.

11. The method of claim 1, further comprising:

identifying a region of pixels surrounding a selected pixel; and calculating a median pixel lag utilizing pixel values corresponding to said region of pixels, said median pixel lag utilized to calculate an excess pixel lag.

12. The method of claim 1, further comprising:

acquiring at least two sets of signals by repeatedly exposing the digital x-ray detector to radiation and reading a set of signals; and calculating an excess pixel lag based on said at least two sets of signals.

13. The method of claim 1, further comprising:

exposing the digital x-ray detector to a first radiation level;

obtaining a first set of signals from pixels in the digital x-ray detector representative of the first radiation level;

exposing the digital x-ray detector to a second radiation level;

obtaining a second set of signals from pixels in the digital x-ray detector representative of the second radiation level, said lag artifact threshold being obtained based on said first and second radiation levels.

14. The method of claim 13, wherein the first radiation level is a high radiation level and the second radiation level is a low radiation level.

15. The method of claim 13, further comprising utilizing a ratio of said first and second radiation levels and an average of pixels surrounding a current pixel to calculate an excess pixel lag for said current pixel, said excess pixel lag representing an amount of lag exceeding said average of pixels.

16. A method for calculating a lag pixel artifact map for a digital x-ray detector, the method comprising:

exposing a digital x-ray detector to radiation;

consecutively reading the digital x-ray detector to obtain at least two sets of pixel values;

obtaining a lag artifact threshold identifying an amount of residual charge that, when held by pixels in the digital x-ray detector, will cause image artifacts;

calculating an excess pixel lag for at least one pixel in the digital x-ray detector; and when said excess pixel lag exceeds said lag artifact threshold, adding said at least one pixel corresponding to said excess pixel lag to a lag pixel artifact map.

17. The method of claim 16, the obtaining step further comprising identifying a perception value determined by perception studies utilized to identify image artifacts.

18. The method of claim 16, wherein said lag artifact threshold is representative of a percent confidence that said at least one pixel will not exhibit an image artifact.

19. The method of claim 16, the calculating step further comprising:

identifying a first pixel in a first set of pixel values; and identifying a second pixel in a second set of pixel values corresponding to said first pixel, wherein said first and second pixels are utilized to calculate said excess pixel lag.

20. The method of claim 19, the identifying a second pixel step further comprising identifying a third pixel in a third set of pixel values corresponding to said first pixel, wherein said first and third pixels are utilized to calculate said excess pixel lag.

21. The method of claim 16, wherein a second set of pixel values is acquired within 200 ms after acquiring a first set of pixel values.

22. The method of claim 16, further comprising:

identifying a noise value determined by noise experienced by said detector; and identifying a radiation level corresponding to said radiation, and utilizing said noise value and said radiation level to calculate said excess pixel lag.

23. The method of claim 16, the obtaining step further comprising utilizing at least one perception value determined by perception studies to calculate at least one said lag artifact threshold.

* * * * *